United States Patent
Anderson

(10) Patent No.: US 10,359,018 B2
(45) Date of Patent: Jul. 23, 2019

(54) INTERLOCK DEVICE FOR START-STOP ENABLED VEHICLES

(71) Applicant: Thomas M. Anderson, Wichita, KS (US)

(72) Inventor: Thomas M. Anderson, Wichita, KS (US)

(*) Notice: Subject to any disclaimer, the term of this patent is extended or adjusted under 35 U.S.C. 154(b) by 0 days.

(21) Appl. No.: 15/936,087

(22) Filed: Mar. 26, 2018

(65) Prior Publication Data

US 2019/0178218 A1 Jun. 13, 2019

Related U.S. Application Data

(60) Provisional application No. 62/613,606, filed on Jan. 4, 2018, provisional application No. 62/598,044, filed on Dec. 13, 2017.

(51) Int. Cl.
| | |
|---|---|
| F02N 11/08 | (2006.01) |
| F02N 11/10 | (2006.01) |
| B60K 28/06 | (2006.01) |
| A61B 5/08 | (2006.01) |

(52) U.S. Cl.
CPC ........ *F02N 11/0822* (2013.01); *B60K 28/063* (2013.01); *F02N 11/101* (2013.01); *A61B 5/082* (2013.01)

(58) Field of Classification Search
CPC . F02N 11/0822; F02N 11/101; B60K 28/063; A61B 5/082
See application file for complete search history.

(56) References Cited

U.S. PATENT DOCUMENTS

| | | | | |
|---|---|---|---|---|
| 4,645,939 | A * | 2/1987 | Robinson | B60R 25/04 123/179.1 |
| 4,689,603 | A * | 8/1987 | Conigliaro | B60K 28/063 307/10.4 |
| 4,697,666 | A * | 10/1987 | Collier | B60K 28/063 180/272 |
| 6,647,328 | B2 * | 11/2003 | Walker | B60R 25/02 701/2 |
| 7,256,700 | B1 | 8/2007 | Ruocco et al. | |
| 7,934,577 | B2 | 5/2011 | Walter et al. | |
| 8,640,813 | B2 | 2/2014 | Doinoff et al. | |
| 9,061,680 | B2 | 6/2015 | Dalum | |
| 9,481,245 | B2 | 11/2016 | Nelson | |

(Continued)

OTHER PUBLICATIONS

Installation Manual for 1st 228-LC Breath Alcohol Ignition Interlock Devices.

(Continued)

*Primary Examiner* — Hung Q Nguyen
*Assistant Examiner* — Brian P Monahon
(74) *Attorney, Agent, or Firm* — Hovey Williams LLP

(57) ABSTRACT

An ignition interlock assembly (74), including an ignition interlock device (10) and a logic circuit controller (68), ensures that a vehicle equipped with assembly (74) and a start-stop functionality will maintain the normal operation of the vehicle even in the event that a failed rolling retest (50, 52*b*) occurs when the start-stop functionality is engaged. The controller (68) preferably includes a pair of normally-opened, interconnected relays which remain energized throughout the operation of the vehicle.

12 Claims, 4 Drawing Sheets

(56) References Cited

U.S. PATENT DOCUMENTS

| | | | | |
|---|---|---|---|---|
| 2004/0083031 | A1* | 4/2004 | Okezie | A61B 5/145 701/1 |
| 2007/0144812 | A1* | 6/2007 | Stewart | B60K 28/063 180/272 |
| 2010/0012417 | A1* | 1/2010 | Walter | B60K 28/063 180/272 |
| 2010/0274411 | A1* | 10/2010 | Ozaki | B60K 28/063 701/1 |
| 2010/0294583 | A1* | 11/2010 | Biondo | B60K 28/063 180/272 |
| 2010/0312431 | A1* | 12/2010 | Kaschner | B60K 28/063 701/31.4 |
| 2010/0314190 | A1* | 12/2010 | Zimmermann | A61B 5/18 180/272 |
| 2011/0309932 | A1* | 12/2011 | Arringdale | B60K 28/063 340/539.14 |
| 2012/0268259 | A1 | 10/2012 | Igel et al. | |
| 2013/0169442 | A1* | 7/2013 | Ruocco | B60K 28/063 340/576 |
| 2014/0297111 | A1* | 10/2014 | Takahashi | B60K 28/06 701/36 |
| 2016/0137164 | A1* | 5/2016 | Jones | F02D 41/0097 701/112 |
| 2017/0096145 | A1* | 4/2017 | Bahn | E05F 15/70 |
| 2017/0096146 | A1* | 4/2017 | Jones | B60W 40/08 |

OTHER PUBLICATIONS

Dräger Interlock XT Installation Manual V3.0 2013.
Hybrid Module—Installation. 2012.
Intoxalock Installation Manual. 2016.
"How Do Eco Cars Affect Ignition Interlocks." Smart Start Brochure, 2018.

* cited by examiner

INTERLOCK DEVICE FOR START-STOP ENABLED VEHICLES

CROSS-REFERENCE TO RELATED APPLICATIONS

This application claims the benefit of application Ser. 62/598,044, filed Dec. 13, 2017, and of application Ser. 62/613,606, filed Jan. 4, 2018. The entireties of these two applications are fully incorporated by reference herein.

BACKGROUND OF THE INVENTION

Field of the Invention

The present invention is broadly concerned with ignition interlock assemblies having rolling retest capabilities designed for connection with vehicles having an ignition, a starter, an engine, and a start-stop function. More particularly, the invention is concerned with such assemblies, as well as logic circuit controllers used therein, which allow the unimpeded restart of the vehicle engine in the event that, during a rolling retest failure, the vehicle's engine is stopped owing to operation of the stop-start function.

Description of the Prior Art

Ignition interlock devices (IID's) are commonly used to prevent vehicle operation in the event that the drivers are impaired or unauthorized. These devices can be used to test a number of driver parameters such as fingerprints, skin characteristics, retina scans, or facial recognition. However, the most common IID's are designed to test the blood alcohol content (BAC) of a given driver and are commonly referred to as BAIID's.

Typical BAIID's include two components. One is a handheld exhalation breathalyzer device that contains an ethanol-specific fuel cell which is operable to determine a driver's blood alcohol content. The other component is a relay box that relays the information and data from the breathalyzer to a command station operatively coupled with ignition, starter, and engine of a vehicle. During an initial start-up of the vehicle, the driver blows into the breathalyzer, and the BAC information is transmitted to the command station. If this data is acceptable, (i.e., the driver is not alcohol-impaired), the command station allows normal operation of the vehicle. However, if the data is unacceptable, the station prevents starting and operating the vehicle.

Most modern-day BAIID's also include a "rolling retest" function. This involves a request via the command station for another test of the driver's BAC after a short time, such as ten minutes, after the initial vehicle start. This is done to prevent a driver from having a non-impaired passenger or other individual provide the first exhalation into the breathalyzer, as a way of circumventing the BAIID During a rolling retest, the driver must again exhale into the breathalyzer within a preset time period. If this second breathalyzer test results in a failure or the driver refuses to provide the second breathalyzer test, the command station notes this as a violation. However, and very importantly, in this situation, the command station does not stop the operation of the vehicle. Such result can be very dangerous if the driver is in heavy traffic or another compromising situation. Rather than stop the vehicle, the command station may initiate an alarm, such as by blowing the vehicle horn and or intermittently blinking the vehicle's headlights.

In recent years, vehicles have been equipped with start-stop technology. This is designed to provide maximum fuel economy and serves to turn off the vehicle engine at stop lights or when the brakes are applied to fully stop the vehicle. In such cases, the vehicle engine is turned off, but automatically restarts when the brake pedal is no longer depressed, or the accelerator is engaged.

A significant problem arises when an IID is installed on a start-stop enabled vehicle. Specifically, if a rolling retest is requested during a time when a vehicle's engine is stopped owing to the operation of the start-stop functionality, the IID will prevent normal restart of the engine by the start-stop apparatus. That is, the IID will operate as it does during the initial start sequence, overriding attempted restart by the start-stop apparatus. This is an extremely dangerous outcome, and Federal Regulations require that IID's cannot interfere with normal vehicle operation after the initial start sequence.

There is accordingly a real and unsatisfied need in the art for ignition interlock assemblies which can provide all of the needed operation during initial starting and rolling retests, and which accommodate the concurrent operation of start-stop apparatus.

Related references include U.S. Pat. Nos. 7,256,700, 7,934,577, 8,640,813, 9,061,680, and 9,481,245; US Patent Publication No. US2012/0268259; and a Smart Start Inc. article entitled "How Do Eco Cars Affect Ignition Interlocks?".

SUMMARY OF THE INVENTION

The present invention overcomes the problems outlined below and provides an improved ignition interlock assembly designed for connection with a vehicle having an engine, an ignition, a starter, and a start-stop function. The interlock assembly includes an ignition interlock device adapted for connection with the vehicle engine, ignition, and starter, the interlock device having a driver parameter input and operable to receive a driver parameter during a rolling retest, and to determine if said driver parameter is acceptable (pass) or unacceptable (fail). The assembly further has a logic circuit controller operatively coupled with the interlock device, ignition and starter. The controller comprises a logic circuit operable to allow the unimpeded restart of the vehicle engine by the start-stop function, in the event that the rolling retest driver parameter is unacceptable, when the vehicle engine is stopped by virtue of the operation of the start-stop function. In this way, the normal operation of the vehicle is assured in such a situation, in accordance with Federal regulations.

The logic circuit controller can be implemented in various ways, but preferably it comprises at least one relay, and more preferably a pair of interconnected relays, one of the latter connected with the vehicle ignition, and the other of the relays connected with the starter. Likewise, the ignition interlock assembly can make use of different driver parameter inputs, but the most common input is by way of a breathalyzer operable to determine the blood alcohol content of the driver.

The invention also provides a controller adapted for coupling with a vehicle interlock device connected with the engine, ignition, and starter of a vehicle, where the vehicle is also equipped with a start-stop function. The interlock device includes a driver parameter input operable to receive the driver parameter during a rolling retest and to determine if the driver parameter is acceptable or unacceptable. The controller includes a logic circuit operable to allow the restart of the vehicle engine by the start-stop function, in the event that the rolling retest driver parameter is unacceptable when the vehicle engine is stopped by virtue of the operation of the start-stop function. The controller further has a connection assembly operable to couple the logic circuit with the interlock device, and the engine, ignition, and starter of the vehicle.

DETAILED DESCRIPTION OF THE PREFERRED EMBODIMENTS

Figure 5:
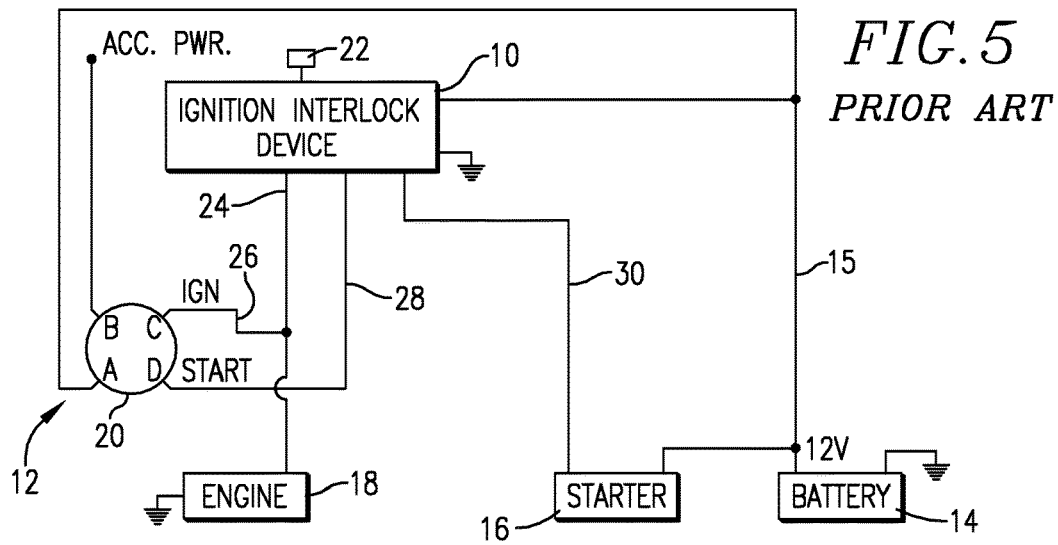
FIG. 5 is a schematic block diagram illustrating a prior art ignition interlock device coupled with the ignition, engine, starter, and battery of a vehicle.
Figure 6:
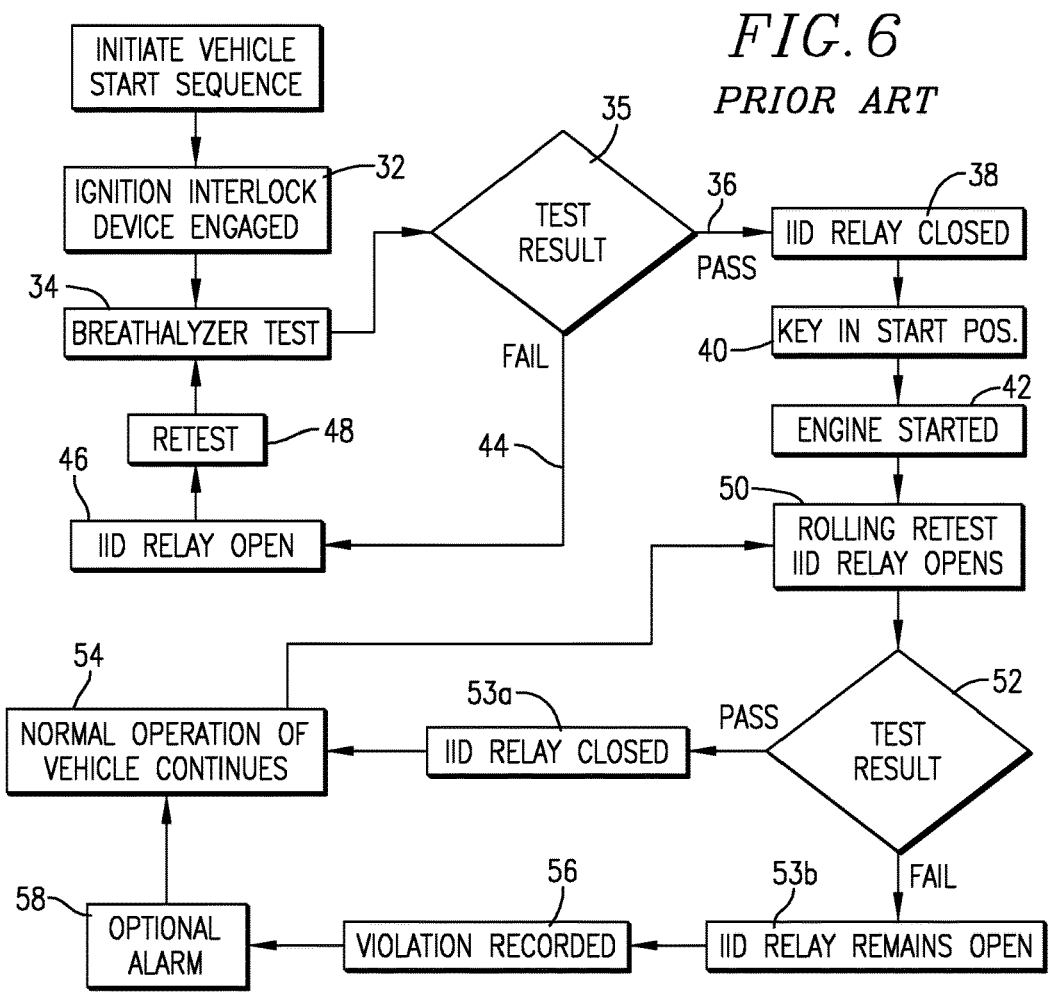
FIG. 6 is a prior art flow diagram illustrating the control sequence of an interlock device coupled with a vehicle not having a start-stop function.
Figure 7:
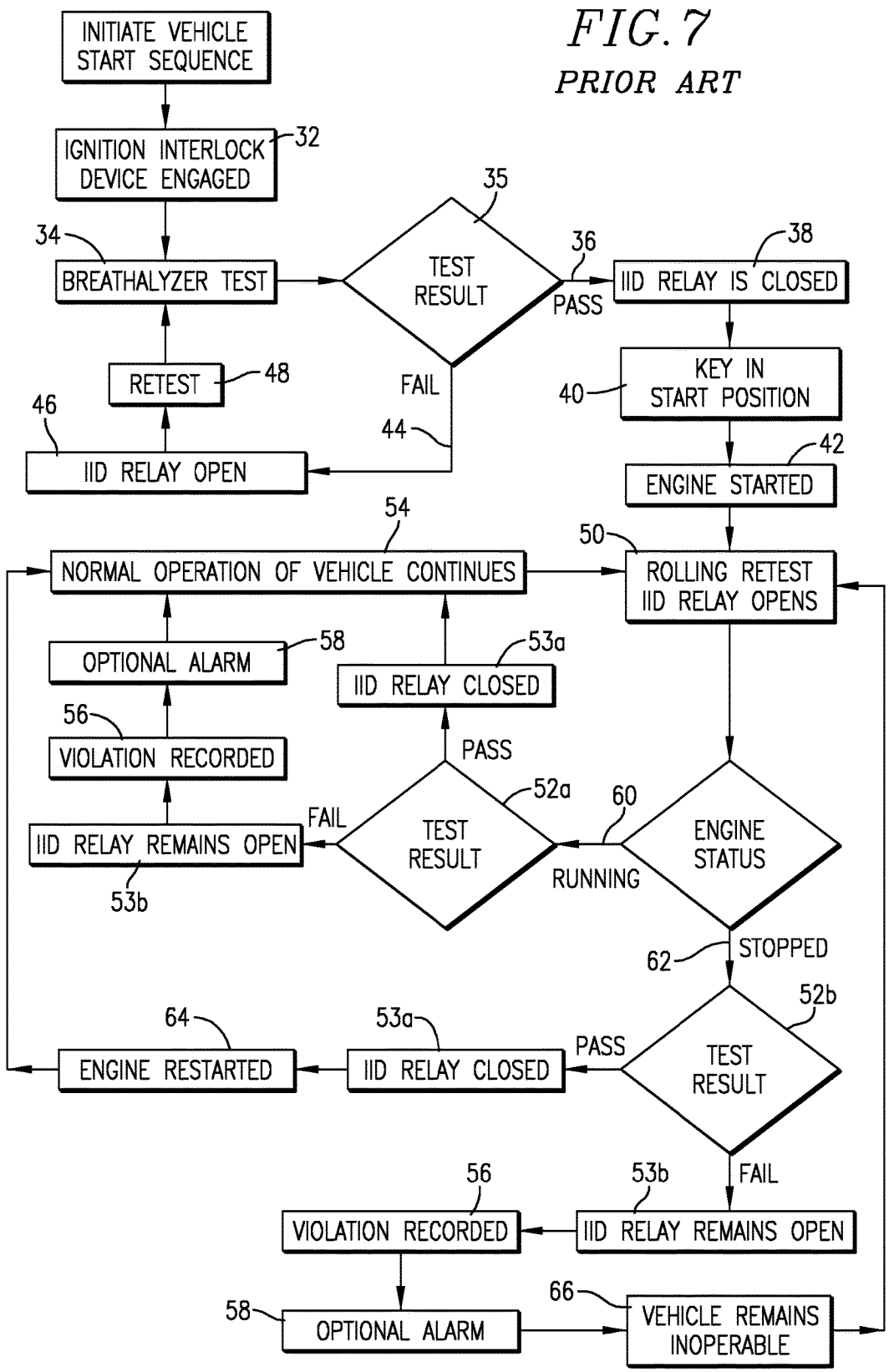
FIG. 7 is a prior art flow diagram illustrating the control sequence of an interlock device coupled with a vehicle having a start-stop function and illustrating the problem of vehicle shutdown in the event of a rolling retest violation during a time when the vehicle engine is stopped via the start-stop function.

The Problem—FIGS. 5-7

FIG. 5 illustrates a conventional ignition interlock device 10 operably coupled with a vehicle ignition system 12, the latter coupled with the vehicle battery 14, starter 16, and engine 18. The ignition system 12 includes a key start module 20 having four positions, namely a position A coupled with battery 14 via lead 15, a position B coupled with accessory power components of the vehicle (e.g., a radio), an ignition position C, and a start position D. As depicted, the interlock device 10 is equipped with a driver parameter input 22 and has conventional internal circuitry designed to receive a driver input parameter (e.g., driver breath) and to determine whether the driver parameter is acceptable or unacceptable. In addition, this circuitry includes a starter actuation circuit which typically includes a switching arrangement such as a normally open control relay (referred to below for exemplary purposes as the "IID Relay"), which is operable to permit initial starting of the engine 18 if the driver parameter is acceptable (IID Relay closes), or to prevent initial starting thereof if the parameter is unacceptable (IID Relay remains open). The circuitry also operates in a rolling retest mode where the IID is opened prior to receiving a second driver parameter from input 22, so as to continue normal operation of the vehicle if the second driver parameter is acceptable (IID Relay is closed), and also to continue such normal operation in the event that the second driver parameter is unacceptable (IID Relay remains open); however, in this event, a violation is recorded, and an optional alarm may be initiated.

As further illustrated in FIG. 5, the interlock device 10 is operably coupled with the engine 18 via lead 24, which is also coupled to position C of ignition module 20 through lead 26. Further, the device 10 is electrically connected with position D of module 20 via lead 28 and to starter 16 via lead 30.

FIG. 6 illustrates the operation of interlock device 10 when coupled with a normal vehicle not having a start-stop function. During this conventional operation, the driver first operates module 20 to position C, step 32. At this point, the driver enters the appropriate parameter by means of input 22 (in the case of a breathalyzer, blowing into an attached breathing tube) as reflected in step 34, results of which are analyzed, step 35. If the test result is acceptable, step 36, the interlock starter actuation circuit is energized, step 38, i.e., IID Relay closes, step 38, and the driver can then operate module 20 to start position D, step 40. The engine 18 can then be started in the normal fashion, step 42. However, if the inputted parameter is unacceptable, step 44, the IID Relay remains open, step 46. The driver must then perform a retest, step 48, by then inputting another driver parameter via input 22. This procedure continues until the parameter is acceptable, and steps 38-42 can be completed.

The device 10 also includes a rolling retest function, step 50, which involves a request from the device 10 for the input of a second driver parameter and the IID Relay is opened. This parameter is then tested with the result determination at step 52. If the second parameter is acceptable, the IID Relay is closed, step 53a, and device 10 permits normal operation of the vehicle, step 54, which allows for subsequent rolling retests as required. If the second parameter is unacceptable, the device 10 records this as a violation, step 56, and may initiate an alarm, step 58. However, and very importantly, even if the rolling retest results in an unacceptable second parameter, the IID Relay remains open, step 53b, and normal operation of the vehicle continues, as required by federal regulations.

FIG. 7 illustrates the operation of the conventional interlock device 10 in connection with a vehicle equipped with a start-stop function. Many of the steps of operation are identical with those of FIG. 6, particularly in the initial start sequence, and accordingly the same reference numerals from FIG. 6 have been used where appropriate.

In particular, the problem arises during the rolling retest, step 50, when the engine 18 has been stopped by virtue of the operation of the start-stop function of the vehicle, and the IID Relay opens. Thus, during the rolling retest, if the engine is running, step 60, the test result, step 52a, is acceptable, the IID Relay is closed, step 53a, and normal operation of the vehicle continues, step 54. Likewise, if the test result, step 52a, is unacceptable, a violation is recorded, step 56, the optional alarm may be activated, step 58, and the IID Relay remains open, step 53b, and normal operation continues, step 54.

However, if the engine status during the rolling retest is stopped, step 62, the test result, step 52b, becomes crucial. If the test result is acceptable, the IID Relay is closed, step 53a, and device 10 allows the engine 18 via the start-stop function to be restarted, step 64, and normal operation of the vehicle continues, step 54. On the other hand, if during this engine-stopped condition the test result 52b is unacceptable, a violation is recorded, step 56, the optional alarm may be activated, step 58, but the IID Relay remains open, step 53b, and the vehicle remains inoperable, step 66. As explained above, this can be an extremely dangerous situation, where the vehicle may be in heavy traffic, and the driver is unable to normally operate the vehicle. How to solve this serious problem is a focus of the present invention.

The following table sets forth the operating conditions for the vehicle ignition system 12, interlock device 10, and the status of engine 18 during some of the important FIG. 7 steps described above, where "SS" refers to the vehicle's start-stop functionality and "Str. Act. Cir." refers to the IID's starter actuation circuit.

LOGIC TABLE OF PRIOR ART IID OPERATION

| Vehicle with SS and IID FIG. 7 | Vehicle Ignition | BAC Test Result | Ignition Interlock Device Str. Act. Cir. | Engine Status |
|---|---|---|---|---|
| Key in OFF position A | Off | N/A | Open | Off |
| Key in ignition position C, Step 32 | On | N/A | Open | Off |
| IID test passed, Steps 35, 36, 38 | On | Pass | Closed | Off |
| Key in start position D, Steps 40, 42 | On | N/A | Closed | On |
| Rolling IID retest requested, Step 50 | On | N/A | Open | On or Off |
| Engine Off, Steps 62, 52b | On | N/A | Open | Off |
| Rolling IID retest passed, Steps 52b, 53a, 64 | On | Pass | Closed | On |
| Rolling IID retest failed, Steps 52b, 53b, 66 | On | Fail | Open | Off* |

*This is the dangerous condition of Step 66 where the vehicle remains inoperable after a failed rolling retest when the vehicle is stopped owing to the operation of the start-stop functionality.

The Invention—FIGS. 1-4

Figure 4:
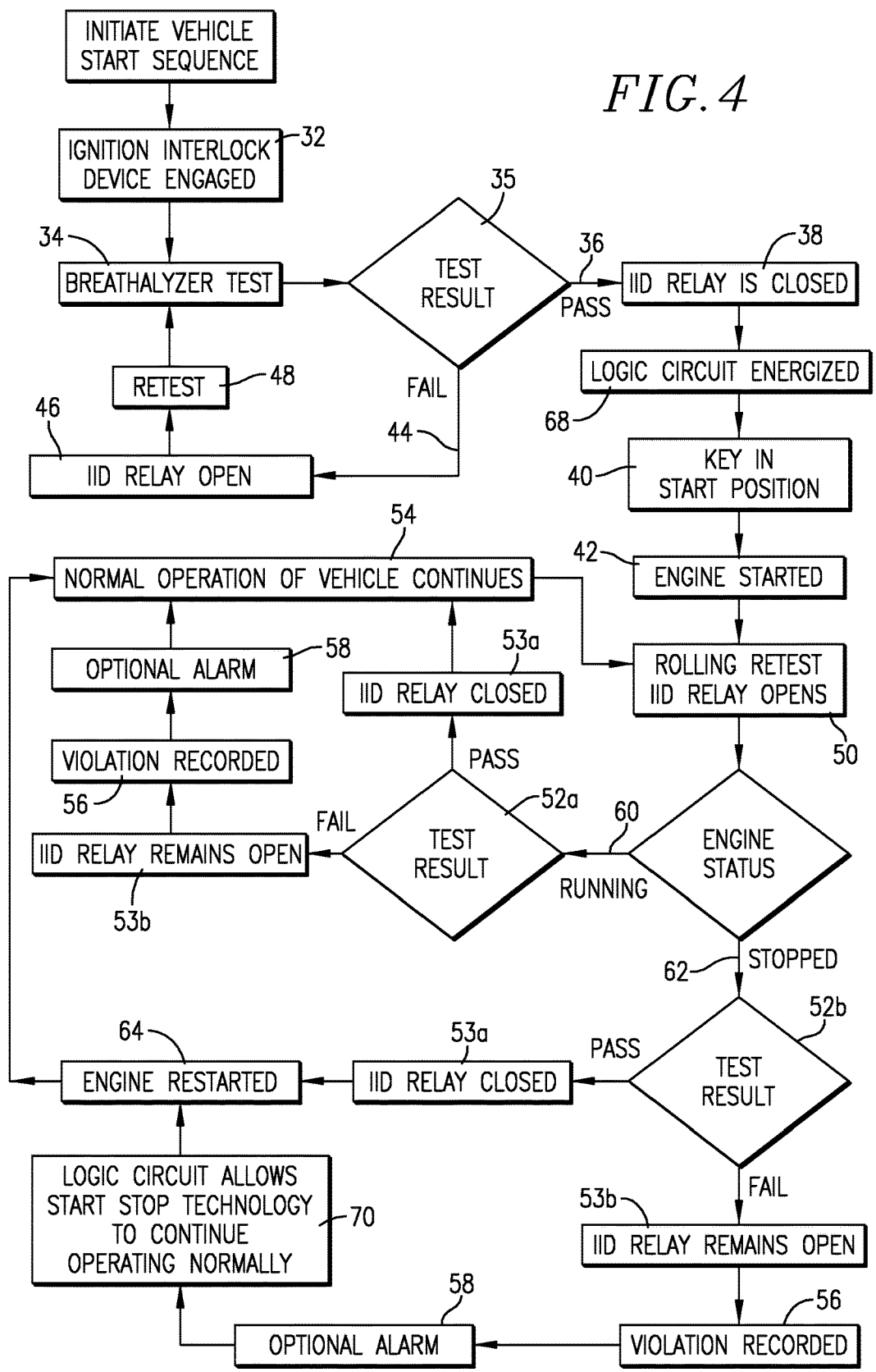
FIG. 4 is a flow diagram illustrating the control sequence of the interlock device and the logic circuit controller of the invention, with a vehicle equipped with a start-stop function.

Generally speaking, the present invention provides a logic circuit controller 68, which is operably coupled with a conventional ignition interlock device 10 to overcome the problem described above, and particularly the issue of a rolling retest failure during a time when the vehicle's engine is stopped because of the action of the start-stop functionality of the vehicle. Specifically, the logic circuit controller 68 permits the engine 18 to be restarted normally by the start-stop functionality so as to permit continued normal operation of the vehicle even during such a vehicle engine stopped rolling retest failure scenario. FIG. 4 illustrates this result through the use of a flow diagram. Again, many of the steps in FIG. 4 are similar to those of FIG. 7, and the same reference numerals have been applied where appropriate. Basically, the difference is that during test result, step 52b, when the engine is stopped, the logic circuit controller 68 operates to allow restart of the engine via the start-stop function, step 70.

Figure 1:
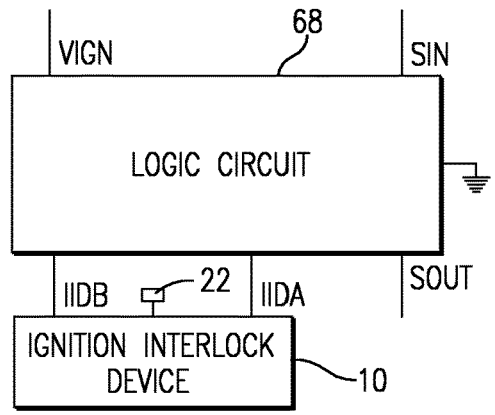
FIG. 1 is a schematic block diagram illustrating a conventional ignition interlock device having a logic circuit controller in accordance with the invention coupled with the interlock device.
Figure 2:
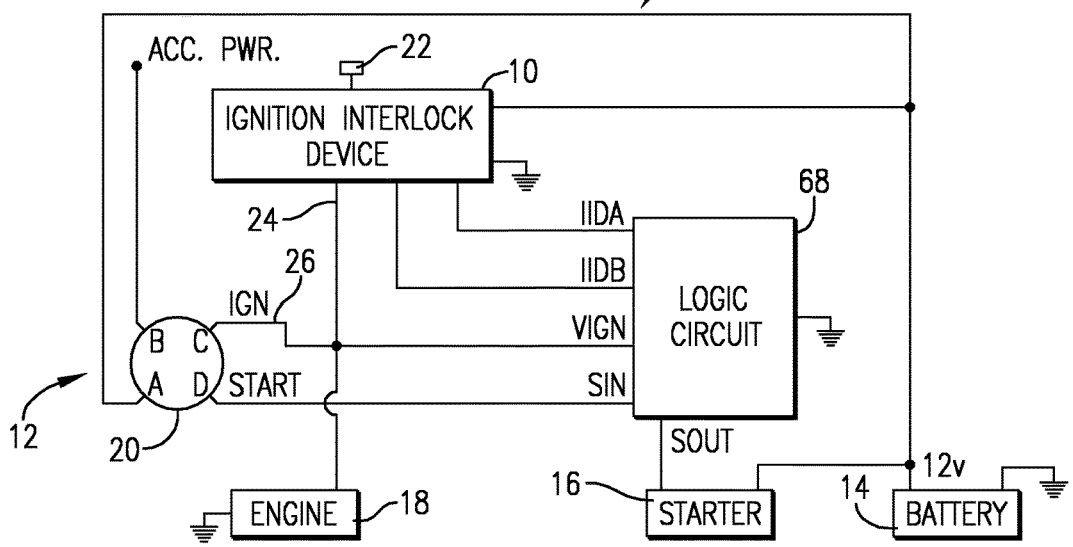
FIG. 2 is a schematic block diagram illustrating representative interconnections between the ignition, engine, starter, and battery of a vehicle, with the interlock device and the logic circuit controller.

The logic circuit controller 68 is operatively connected to the ignition interlock device 10 and is interposed between the device 10, the ignition system 12, starter 16, and engine 18. Turning first to FIG. 1, two leads labeled IIDA and IIDB are coupled between the device 10 and controller 68. Three other leads, VIGN, SIN, and SOUT are coupled with the circuit 68. VIGN and SIN are connected to the system 12, whereas SOUT is connected to the starter 16. FIG. 2 further illustrates these connections, wherein VIGN is connected to lead 24 and SIN is connected to position D of module 20.

Figure 3:
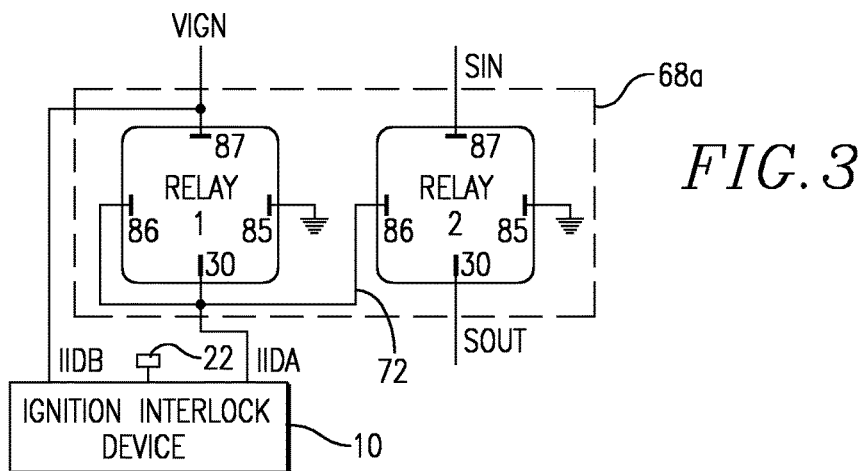
FIG. 3 is a partially schematic block diagram illustrating one implementation of the logic circuit controller illustrated in FIG. 1, making use of a dual relay assembly.

The logic circuit controller 68 can be implemented in a variety of ways such as by the use of conventional relays, electronic circuitry, or software control. One such implementation is illustrated in FIG. 3, wherein a relay-type logic circuit controller 68a is depicted. The controller 68a is equipped with a pair of standard, normally open automotive relays, namely relay 1 and relay 2. As illustrated, each of these relays has standard coil terminals 86 and 85, and corresponding load terminals 87, 30. In this example, it will be observed that lead IIDB is connected with load terminal 87 of relay 1, whereas lead IIDA is connected with load terminal 30 of relay 1. Additionally, a connecting lead 72 is coupled between coil terminal 86 of relay 1 and coil terminal 86 of relay 2. Further, lead SIN is connected with load terminal 87 of relay 2, and SOUT is connected with load terminal 30 of relay 2.

The connection of leads IIDD and IIDA to device 10 depend upon particular type of starter actuation circuit used in the device 10. For example, many commercial devices 10 make use of a conventional, normally open automotive relay such as those depicted in FIG. 3. In such a case, IIDA and IIDB would be appropriately connected to the load terminals 87 and 30 of such a circuit.

The operation of the ignition interlock assembly 74 of FIG. 2, using the controller 68a, of FIG. 3, proceeds as follows, with reference to the steps of FIG. 4. First, in step 32, the device 10 is energized when the module 20 is moved to position C. After a successful driver parameter test, steps 35, 36, the IID's starter actuation circuit (in this example, the IID Relay) is energized. This in turn energizes both relay 1 and relay 2 through lead 72. When the module 20 is then moved to position D, the starter 16 is actuated through leads SIN and SOUT, to start the engine 18. Importantly, relay 1 and relay 2 remain energized throughout the entire time the vehicle operates, because the module 20 remains in position C until the engine 18 is intentionally stopped by moving module 20 to position A.

During a rolling retest 50 when the engine 18 remains running (i.e., the start-stop functionality is not engaged), step 52a, this engine running condition remains, step 54, regardless of whether the test is passed or failed. In the case of a rolling retest 50 when engine 18 is stopped (i.e., the start-stop functionality is engaged), step 52b, a successful test causes the IID Relay to close, Step 53a, which allows the engine to be restarted, step 64. Likewise, if the rolling retest, step 52b, is a failure, the IID Relay remains open, step 53b; however, the logic circuit controller 68a, nevertheless, allows the engine 18 to be restarted, step 64. This is made possible by the facts that relay 1 and relay 2 remain energized, through lead 72, allowing normal functionality of the ignition interlock device 10 and the vehicle's start-stop technology. Therefore, this continued engine operation result obtains without any steps or interventions by the driver of the vehicle, i.e., the result is "automatic."

The following table sets forth the operating conditions for the vehicle ignition system 12, ignition interlock device 10, and the status of engine 18 during some of the important FIG. 4 steps described above, where "LC" refers to the logic circuit controller.

LOGIC TABLE FOR LOGIC CIRCUIT CONTROLLER

| Vehicle with SS, IID, and LC FIG. 4 | Vehicle Ignition | BAC Test Result | Ignition Interlock Device Spr. Act. Cir. | Logic Circuit | Engine Status |
|---|---|---|---|---|---|
| Key in OFF position A | Off | N/A | Open | Open | Off |

-continued

LOGIC TABLE FOR LOGIC CIRCUIT CONTROLLER

| Vehicle with SS, IID, and LC FIG. 4 | Vehicle Ignition | BAC Test Result | Ignition Interlock Device Spr. Act. Cir. | Logic Circuit | Engine Status |
|---|---|---|---|---|---|
| Key in ignition position C, Step 32 | On | N/A | Open | Open | Off |
| IID test passed, Steps 35, 36, 38 | On | Pass | Closed | Closed | Off |
| Key in start position D, Steps 40, 42 | On | N/A | Closed | Closed | On |
| Rolling IID retest requested, Step 50 | On | N/A | Open | Closed | On or Off |
| Engine Off, Steps 62, 52b | On | N/A | Open | Closed | On |
| Rolling IID retest passed, Steps 52b, 53a, 64 | On | Pass | Closed | Closed | On |
| Rolling IID retest failed, Steps 52b, 53b, 70, 64 | On | Fail | Open | Closed | On+ |

+On condition during rolling retest failure legal and provides for safe operation of the vehicle.

I claim:

1. An ignition interlock assembly designed for connection with a vehicle having an engine, an ignition, a starter, and a start-stop function, said ignition interlock assembly comprising:
 an ignition interlock device adapted for connection with a vehicle engine, ignition, and starter, said interlock device having a driver parameter input and circuitry operable to receive a driver parameter during a rolling retest, and to determine if said driver parameter is acceptable or unacceptable; and
 a logic circuit controller operatively coupled with said interlock device, ignition and starter, said controller including a logic circuit operable to allow the unimpeded restart of said vehicle engine by the start-stop function, in the event that said rolling retest driver parameter is unacceptable when the vehicle engine is stopped by virtue of the operation of said start-stop function, said unimpeded restart of the vehicle occurring without any steps or interventions by the driver of the vehicle.

2. The ignition interlock assembly of claim 1, said logic circuit comprising at least one relay.

3. The ignition interlock assembly of claim 2, said logic circuit comprising a pair of interconnected relays, one of said relays being connected with said vehicle ignition, and the other of said relays being connected with said ignition and said starter.

4. The ignition interlock assembly of claim 3, both of said relays being energized during said rolling retest regardless of whether the driver parameter is acceptable or unacceptable.

5. The ignition interlock assembly of claim 1, said driver parameter input comprising a breathalyzer for receiving the exhalation of said driver, said interlock operable to determine the blood alcohol content of the driver.

6. A controller adapted for coupling with an interlock device connected with the engine, ignition, and starter of a vehicle, said vehicle equipped with a start-stop function, said interlock device including a driver parameter input operable to receive the driver parameter during a rolling retest, and to determine if the driver parameter is acceptable or unacceptable, said controller comprising:
 a logic circuit operable to allow the restart of said vehicle engine by said start-stop function, in the event that said rolling retest driver parameter is unacceptable when the vehicle engine is stopped by virtue of the operation of said start-stop function, said restart occurring without any steps or interventions by the driver of the vehicle; and
 a connection assembly operably coupling said logic circuit with said interlock device and said engine, ignition, and starter.

7. The controller of claim 6, said logic circuit comprising at least one relay.

8. The controller of claim 7, said logic circuit comprising a pair of interconnected relays, one of said relays connected with said vehicle ignition, and the other of said relays connected with said starter.

9. The controller of claim 8, both of said relays being energized during said rolling retest, regardless of whether the driver parameter is acceptable or unacceptable.

10. The controller of claim 6, said driver parameter input comprising a breathalyzer for receiving the exhalation of said driver, said interlock operable to determine the blood alcohol content of the driver.

11. The controller of claim 8, said connection assembly comprising leads in order to couple said one relay to said vehicle ignition, and additional leads in order to couple said other relay to said starter.

12. The controller of claim 8, each of said relays having a pair of coil terminals and a pair of load terminals, there being a lead between a coil terminal of said one relay, and the coil terminal of said other relay.

* * * * *